United States Patent [19]

Mookherjee et al.

[11] 4,331,611
[45] May 25, 1982

[54] NITRILE AND USES OF SAME IN PERFUMES, COLOGNES AND PERFUMED ARTICLES

[75] Inventors: Braja D. Mookherjee, Holmdel; Richard A. Wilson, Westfield; Frederick L. Schmitt, Holmdel; Manfred H. Vock, Locust, all of N.J.

[73] Assignee: International Flavors & Fragrances Inc., New York, N.Y.

[21] Appl. No.: 199,753

[22] Filed: Oct. 23, 1980

Related U.S. Application Data

[63] Continuation-in-part of Ser. No. 106,158, Dec. 21, 1979, abandoned.

[51] Int. Cl.³ .................... C07C 121/48; C11B 9/00; A61K 7/46; C07C 120/02
[52] U.S. Cl. .................................. 260/464; 560/122; 252/89.1; 252/174.11; 252/522 R; 424/69
[58] Field of Search ......................................... 260/464

[56] References Cited

U.S. PATENT DOCUMENTS 4,100,184 7/1978 Kondo et al. ...................... 260/424

FOREIGN PATENT DOCUMENTS 2237872 2/1975 France .
1353898 5/1974 United Kingdom .

OTHER PUBLICATIONS

C.A., 83, (1975), 178423s.
C.A., 87, (1977) 184076e.
Hill, et al., Tetrahedron, 1965, 21, pp. 1501-1507.

Primary Examiner—Joseph Paul Brust

Attorney, Agent, or Firm—Arthur L. Liberman

[57] ABSTRACT

Described is the nitrile having the structure:

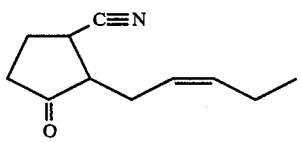

which defines one or a mixture of the isomers:

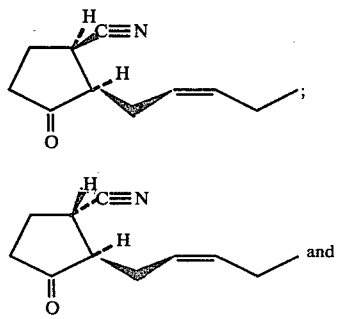

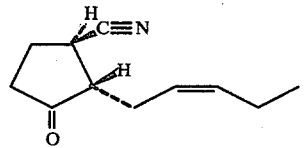

uses thereof as intermediates and in augmenting or enhancing the aroma of perfumes or perfumed articles.

1 Claim, 8 Drawing Figures

GLC PROFILE FOR EXAMPLE I.

NMR SPECTRUM FOR EXAMPLE I.

IR SPECTRUM FOR EXAMPLE I

MASS SPECTRUM FOR EXAMPLE I.

GLC PROFILE FOR EXAMPLE II.
CARBOWAX 20 M COLUMN.

MASS SPECTRUM FOR EXAMPLE II.
CARBOWAX 20M COLUMN

GLC PROFILE FOR EXAMPLE II.
SE-30 COLUMN.

MASS SPECTRUM FOR EXAMPLE II.
SE-30 COLUMN.

NITRILE AND USES OF SAME IN PERFUMES, COLOGNES AND PERFUMED ARTICLES

This application is a continuation-in-part of application for U.S. Letters patent Ser. No. 106,158 filed Dec. 21, 1979 now abandoned.

BACKGROUND OF THE INVENTION

The instant invention provides novel nor-methyl jasmonate having the structure:

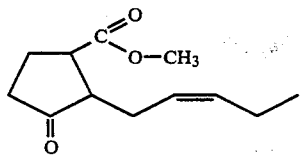

and optical isomers thereof having the structures:

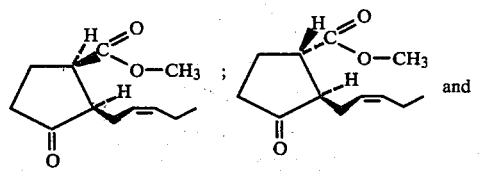

as well the novel intermediates for producing same having the structure:

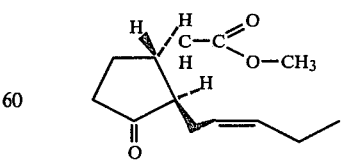

and optical isomers thereof having the structures:

which are also useful in augmenting or enhancing the aroma of perfume compositions, colognes and perfumed articles; as well as processes for preparing same according to the reaction sequence:

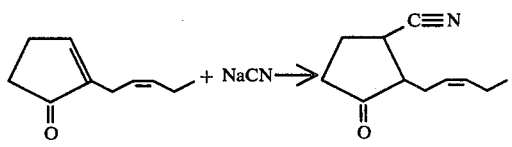

and

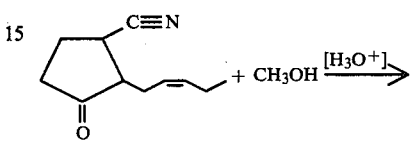

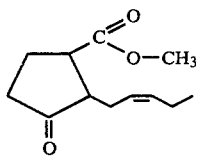

and organoleptic uses of said nor-methyl jasmonate and nitriles for augmenting or enhancing the fresh, clean, jasmine, floral aroma of perfume compositions, colognes and perfumed articles.

Chemical compounds which can provide "fresh, clean" jasmine aromas and which can round out jasmine perfumes and colognes and perfumed articles having jasmine aromas are desirable in the art of perfumery and in the art of detergent manufacture and fabric softener manufacture. Many of the natural materials which provide the jasmine fragrance and contribute such desired nuances to perfumery compositions are high in cost, e.g., jasmine absolute; they are unobtainable at times, vary in quality from one batch to another and/or are generally subject to the usual variations of natural products.

There is, accordingly, a continuing effort to find synthetic materials which will aid in replacing, enhancing or augmenting the essential fragrance notes provided by natural jasmine oil or jasmine absolute. Unfortunately, many of the synthetic materials either have the desired nuances only to a relatively small degree or else contribute undesirable or unwanted odor to the compositions. The search for materials which can provide a more refined jasmine aroma has been difficult and relatively costly in the areas of both natural products and synthetic products.

Methyl jasmonate having the structure:

has an important use in the aroma in perfume compositions and perfumed articles of jasmine absolute. The absolute configuration of methyl jasmonate was published in Tetrahedron, 1965, Vol. 21, pages 1501 to 1507.

Alkyl-2-alkyl-3-oxacyclopentan carboxylates are described for use for their floral and woody aroma nuances in perfumes in British Pat. No. 1,353,898. These compounds have the generic structure:

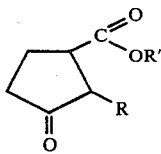

wherein R represents branched or straight chain alkyl or cycloalkyl having from 4 up to 8 carbon atoms and R' represents methyl or ethyl. These compounds are indicated to be prepared using the compound having the structure:

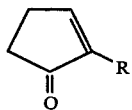

as a starting material, reacting it with HCN or a HCN precursor to form the compound having the structure:

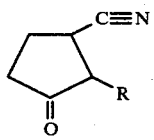

and then reacting that compound with an alcohol in the presence of an acid catalyst. The reaction sequence set forth in British Patent Specification 1,353,898 is as follows:

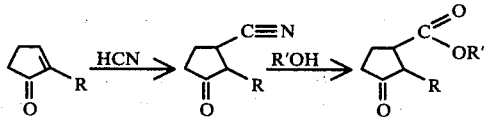

French Pat. No. 7,326,210 issued on Feb. 14, 1975 discloses a genus of compounds including the compound having the structure:

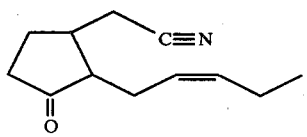

and indicates that this genus is useful in perfumery but does not specifically disclose the compound having the structure:

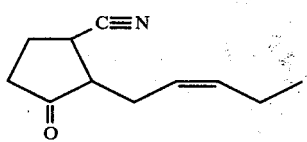

for use in perfumery. In any event, the compounds having the structures:

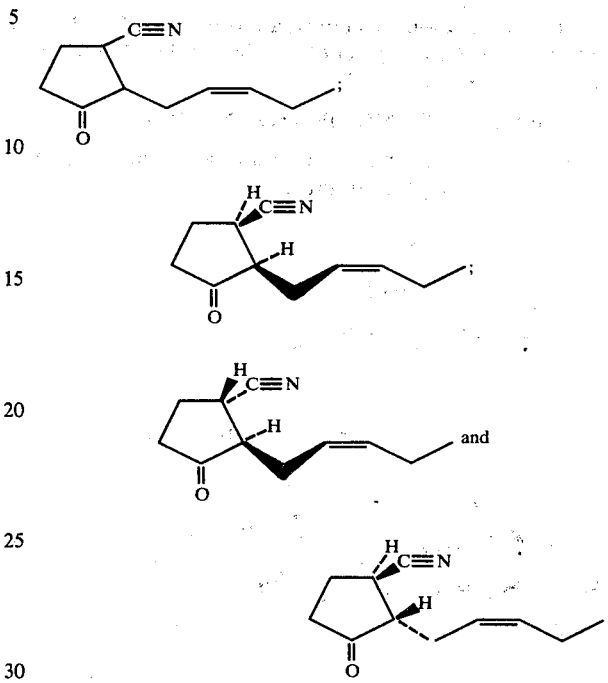

and have unexpected, unobvious and advantageous properties when compared to the compound having the structure:

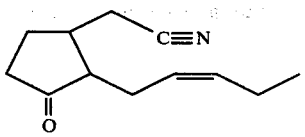

Furthermore, nothing in the prior art, however, in either British Pat. No. 1,353,898 or in any other prior art discloses the compound having the structure:

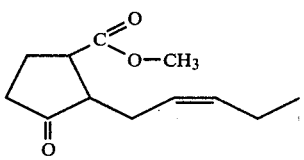

or its stereoisomers or intermediates for preparing same having the structure:

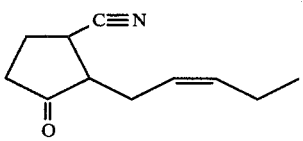

or processes for preparing such compounds according to the reaction sequence:

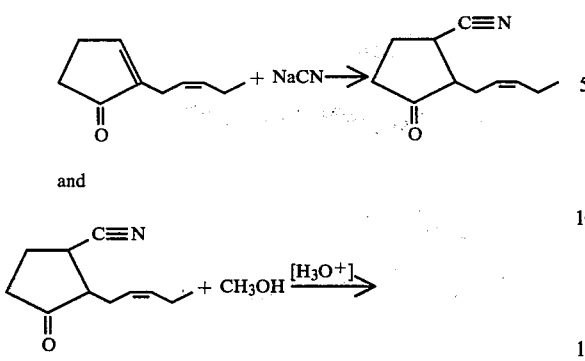

and

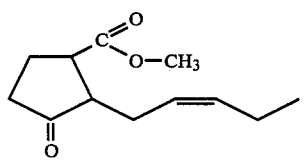

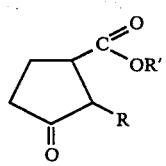

The compound having the structure:

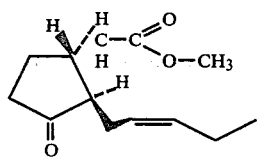

and the stereoisomers thereof have properties unexpected, unobvious and advantageous in perfumery and in perfumed articles with respect to compounds having the generic structure:

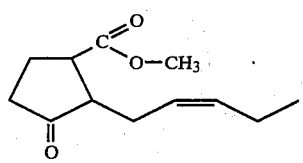

wherein R and R' are defined as above or methyl jasmonate itself having the structure:

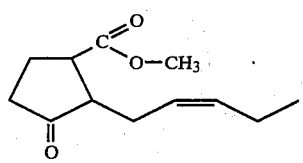

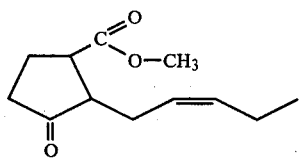

Figure 2:
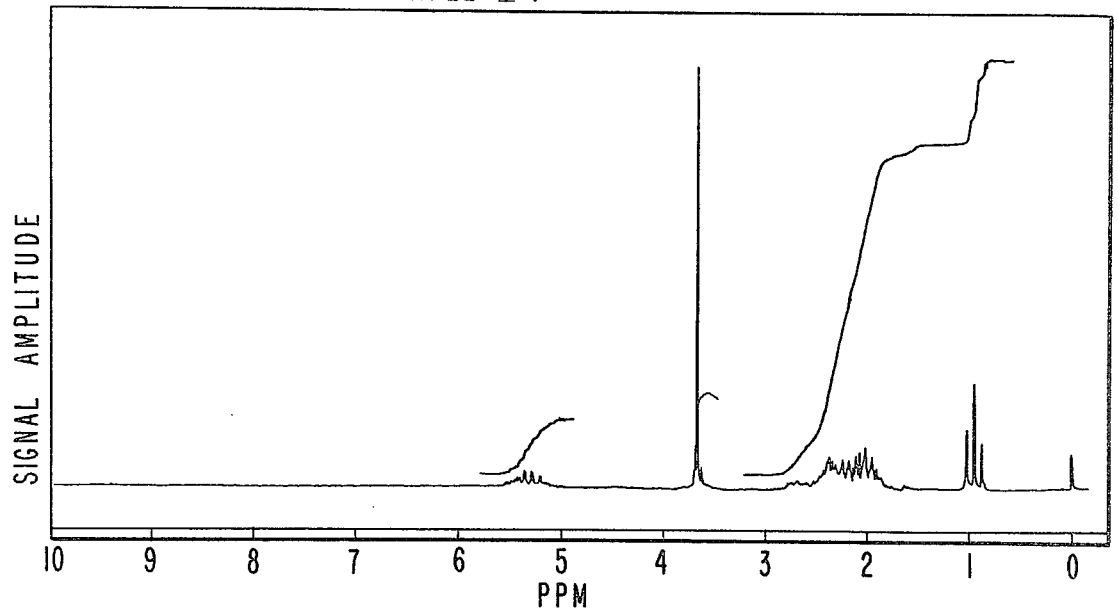

FIG. 2 is the NMR spectrum for nor-methyl jasmonate produced according to Example I having the structure:

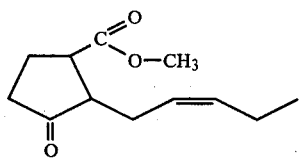

Figure 3:
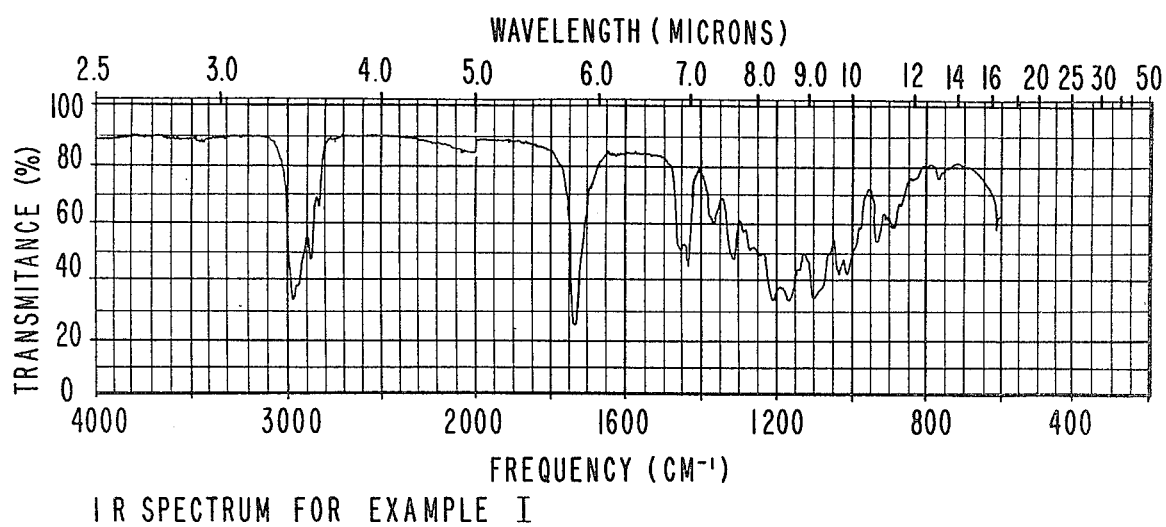

FIG. 3 is the infrared spectrum for nor-methyl jasmonate having the structure:

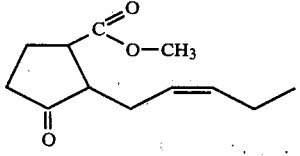

produced according to Example I.

Figure 4:
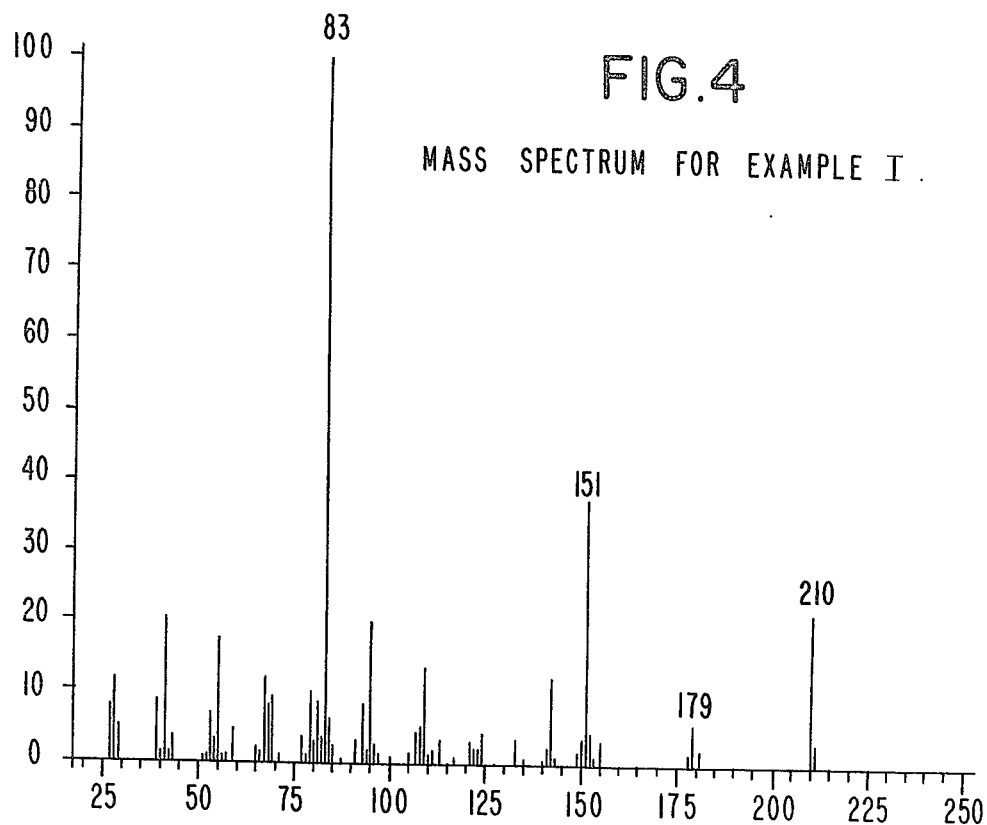

FIG. 4 is the mass spectrum for nor-methyl jamonate having the structure:

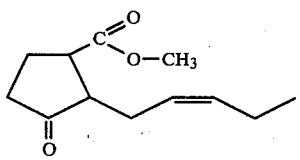

produced according to Example I.

Figure 5:
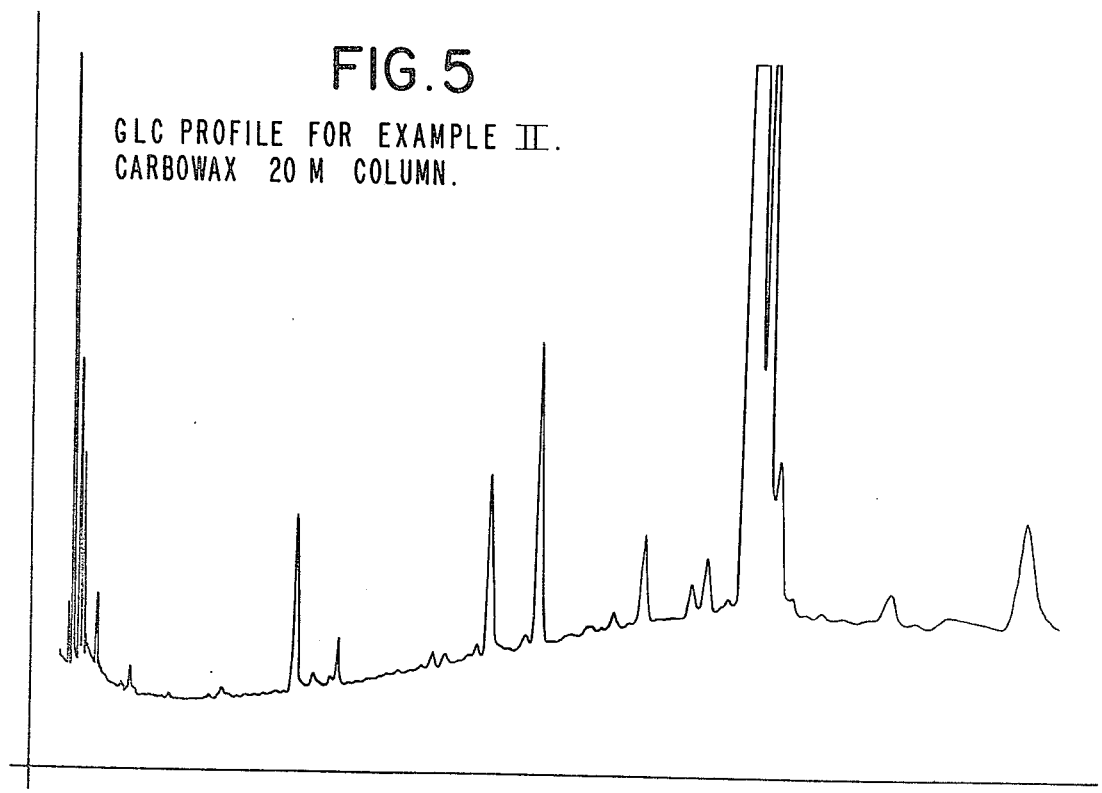

FIG. 5 is the GLC profile (using a carbowax 20-M column) for jasmine absolute carbonyls containing nor-methyl jamonate having structure:

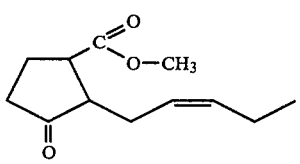

Figure 6:
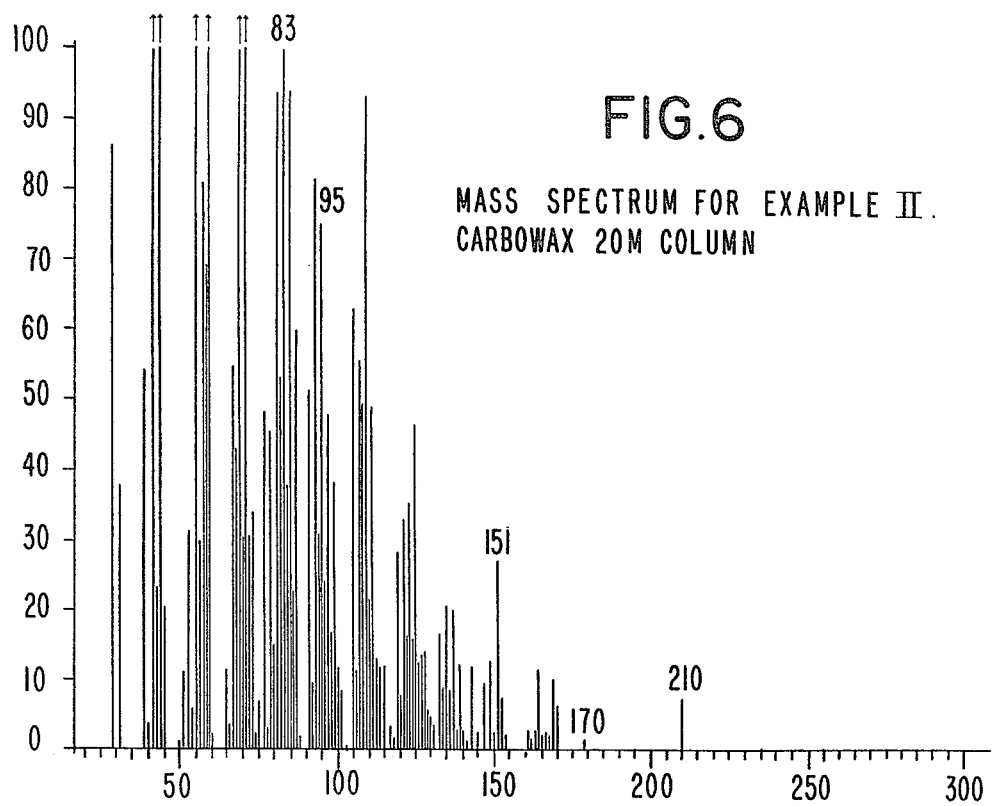

FIG. 6 is the mass spectrum for nor-methyl jasmonate having the structure:

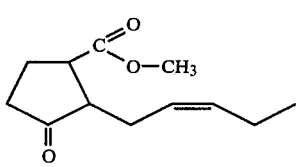

obtained from jasmine absolute carbonyls according to Example II (GLC Carbowax 20-M trapping).

Figure 7:
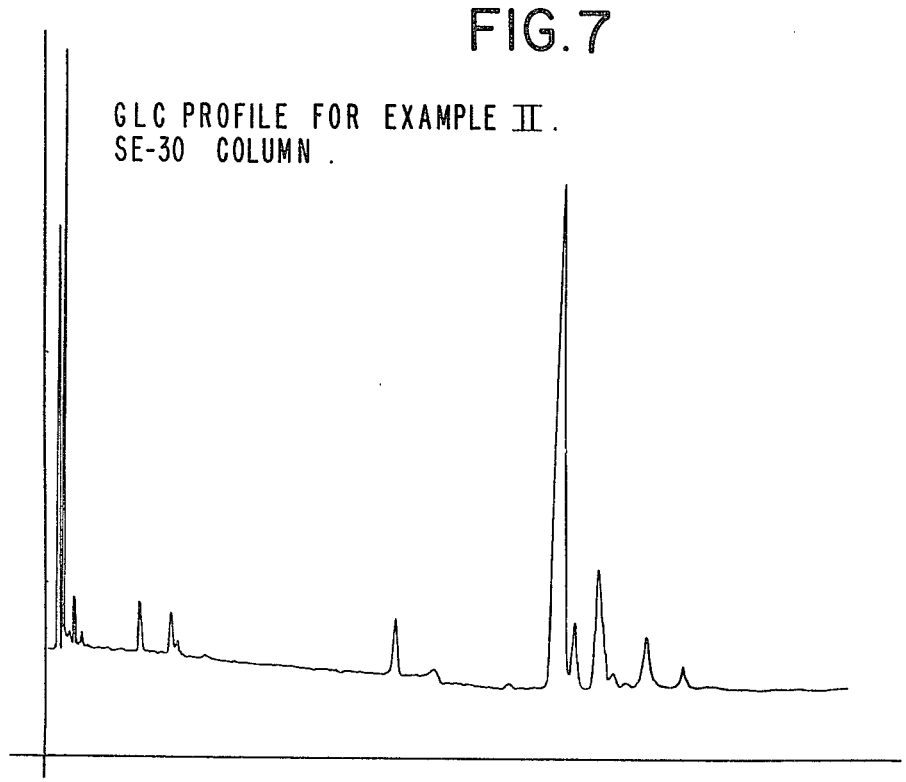

FIG. 7 is the GLC profile (SE-30 column) of jasmine absolute carbonyls containing nor-methyl jasmonate having the structure:

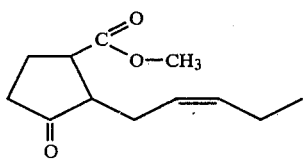

produced according to Example II.

Figure 8:

FIG. 8 is the mass spectrum for nor-methyl jasmonate having the structure:

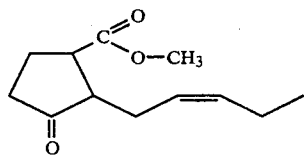

trapped from the GLC trapping (from the SE-30 column) produced according to Example II.

THE INVENTION

This invention relates to nor-methyl jasmonate having the structure:

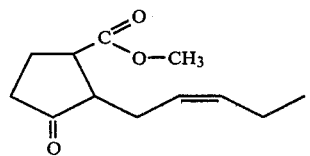

stereoisomers thereof having the structures:

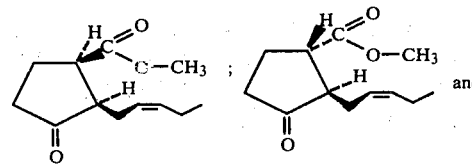

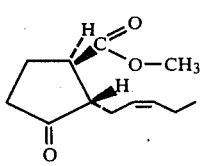

intermediates used in preparing same having the structure:

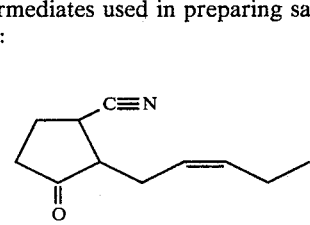

and stereoisomers thereof having the structures:

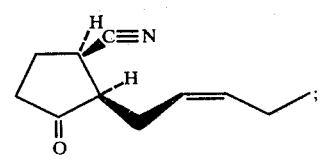

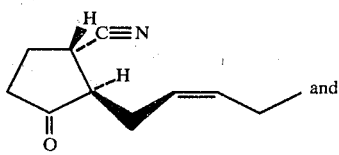

and

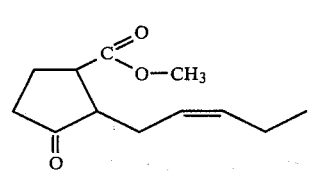

which nitriles are also useful in augmenting or enhancing the aroma of perfumes, colognes and perfumed articles; and processes for preparing said nor-methyl jasmonate according to the reaction sequence:

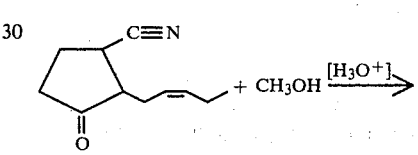

and

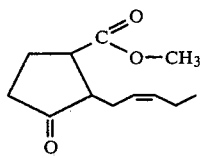

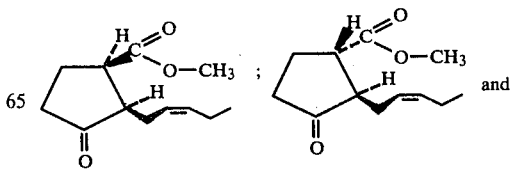

as well as organoleptic uses of said nor-methyl jasmonate and nitriles in augmenting or enhancing the jasmine aroma of perfumes, colognes and perfumed articles, such as anionic, cationic and nonionic solid or liquid detergents, fabric softeners such as dryer-added fabric softener articles and fabric softener compositions as well as deodorant compositions.

The nor-methyl jasmonate having the structure:

and its stereoisomers having the structures:

-continued

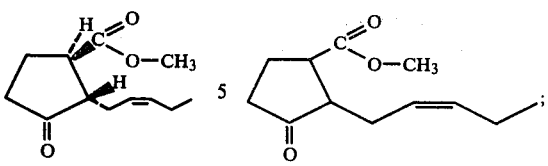

can be prepared by reacting cis-2-pentenyl chloride with 2-cyclopentenone thereby forming 2-(2-cis-pentenyl) cyclopentene-1-one having the structure:

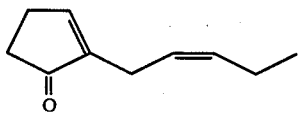

The resulting compound is then reacted with hydrogen cyanide or a hydrogen cyanide precursor to form the nitrile having the structure:

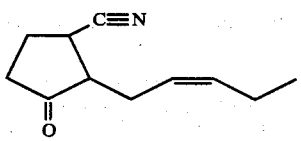

This nitrile, a novel compound, can be used as is for augmenting or enhancing the aroma or taste of consumable materials including perfumes in perfumed articles and colognes or it can be used as an intermediate in its racemic mixture form, or it can be separated into its stereoisomers having the structures:

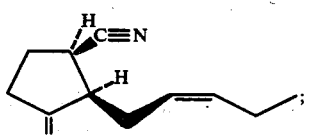

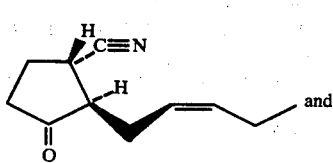

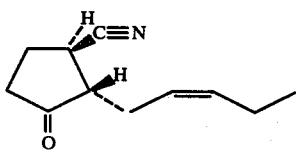

by first reacting the racemic mixture components (in admixture) with an optically active amine to form a mixture of Shiff bases and then separating the mixture of optically active Shiff bases as by fractional crystallization.

The resulting nitrile, either in racemic mixture form or in optical isomer form, may then be reacted with acidic methyl alcohol followed by hydrolysis to form the resulting nor-methyl jasmonate in racemic mixture or in optical isomer form represented by one of the structures:

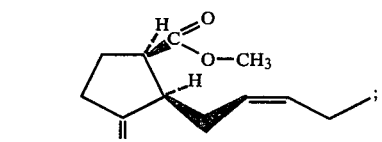

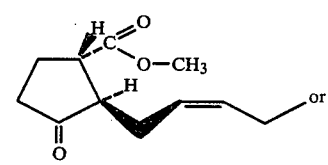

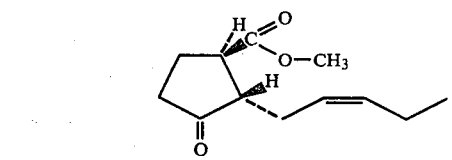

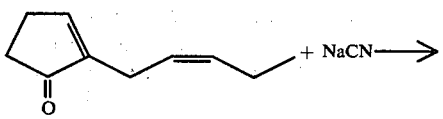

With respect to the reaction:

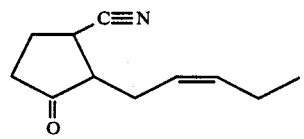

wherein the sodium cyanide can be replaced with another alkali metal cyanide such as potassium cyanide, the reaction temperature should be in the range of from about 20° C. up to about 50° C. with a preferred reaction temperature of 35°-40° C. The mole ratio of 2(2-cis-pentenyl)cyclopentenone-1:hydrogen cyanide or hydrogen cyanide source may vary from 1:1 up to about 1:3 with a mole ratio of ketone:hydrogen cyanide or hydrogen cyanide source preferably being about 1:2. The reaction should take place in acidic media at a pH in the range of from about 4 up to about 6.5. Thus, a weak acid such as formic acid, acetic acid, propionic acid or butyric acid should be present in the reaction medium and the mole ratio of weak acid:2(2-cis-pentenyl)cyclopentenone-1 should be about 1:1. The reaction should take place in the present of an inert solvent in aqueous media, such as 95% aqueous ethanol or 95% aqueous methanol and the concentration of 2(2-cis-pentenyl)cyclopentenone-1 should be between 0.2 and 0.5 moles per liter with a preferred concentration of 0.25-0.35 moles per liter. The concentration of weak acid in the reaction medium should be between 0.2 and 0.5 moles per liter with a preferred mole ratio of 0.25-0.35 moles per liter.

The reaction preferably and conveniently is to take place at atmospheric pressure although superatmospheric and subatmospheric pressures may be used without detrimentally affecting the yield of nitrile having the structure:

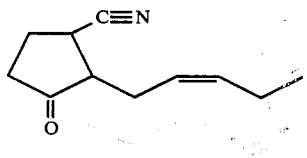

Insofar as the reaction:

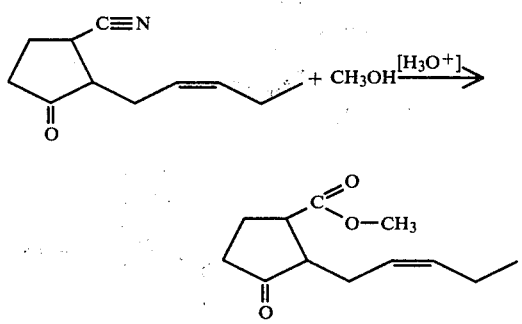

this reaction should take place at a temperature in the range of 90° C. up to 120° C. in the presence of an acid, such as para toluene sulfonic acid or phosphoric acid. It is preferred that the reaction take place at reflux, e.g., 112° C. when using the para toluene sulfonic acid and it is also preferred that the reaction time be between about 4 and about 15 hours. The mole ratio of acid:nitrile having the structure:

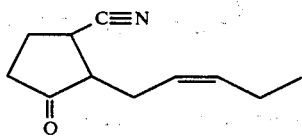

may vary between 0.5:1 and 1:0.5 with the preferred ratio of acid-nitrile being about 1:1. The ratio of methyl alcohol:nitrile having the structure:

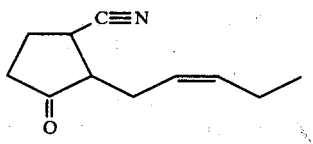

may vary between 0.5:1 and 1:0.5 with a ratio of 1.25 moles of methyl alcohol:1 mole nitrile being preferred. It is also preferred that the reaction take place at atmospheric pressure although higher pressures requiring higher reflux temperatures may be used and lower pressures requiring lower reflux temperatures may also be used so long as the reflux temperature of reaction does not fall below about 90° C. Higher temperatures require a shorter time of reaction and lower temperatures, correspondingly, require longer times of reaction.

At the end of the reaction:

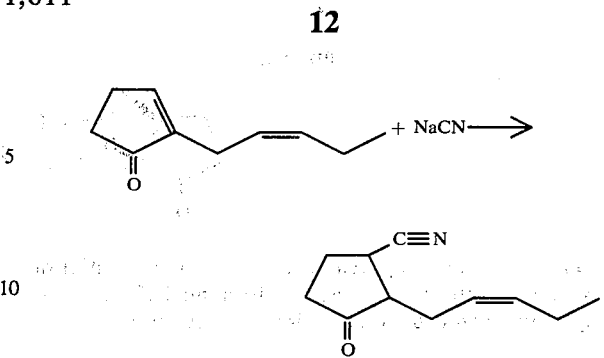

it is preferred that the reaction mass be "worked up" whereby the nitrile having the structure:

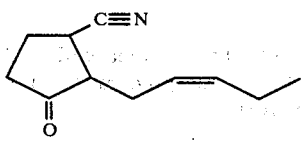

is refined, e.g., by first removing the excess ethanol solvent or other inert solvent and then extracting the aqueous phase with organic solvents, such as diethyl ether; combining the organic phases and neutralizing the resulting organic phases, e.g., with sodium carbonate solution; and then drying the resulting organic phase. This material is then fractionally distilled to yield the desired nitrile. As stated above, the desired nitrile having the structure:

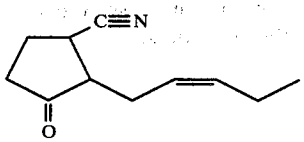

may be separated into its component stereoisomers as by reacting the racemic mixture with optically active amines forming optically active Shiff bases and then fractionally crystallizing out the different Shiff bases and finally acidifying the resulting pure optically active materials reforming the optically active ketones having the structures:

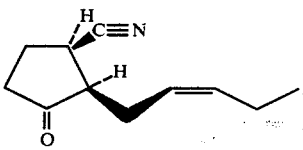

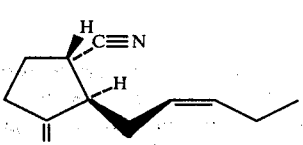

and

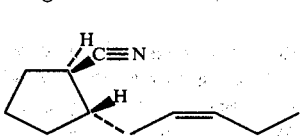

Insofar as the reaction:

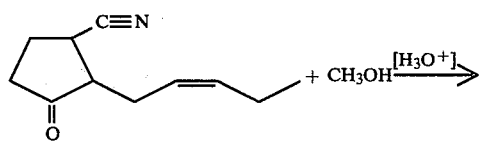 + CH$_3$OH $\xrightarrow{[H_3O^+]}$

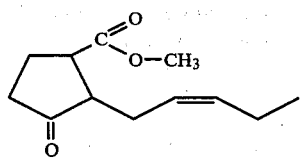

is concerned at the end of the reaction, the reaction mass is "worked up" by pouring the reaction mass onto ice and then taking up the resulting organic layer in inert solvent, such as diethyl ether. The aqueous layer is extracted with diethyl ether and the ether layers are combined and washed thusly neutralized, e.g., with sodium carbonate. The resulting organic layer is then dried over such materials as anhydrous sodium sulfate and subsequently distilled. The foregoing "work up" not only applies to the racemic ester of mixture but also applies to the individual stereoisomer materials which would be made from the stereoisomers of the respective nitriles. Thus, the resulting stereoisomers may have the structures:

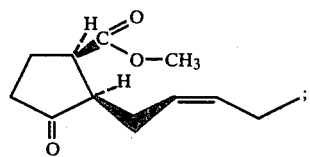;

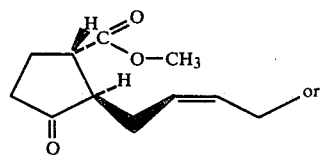 or

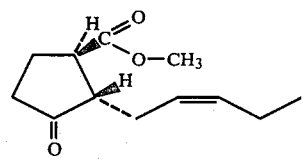

or alternatively the racemate of the compound having the structure:

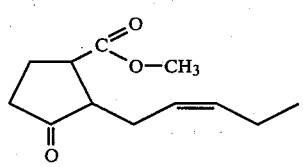

may be reacted with optically active amines to produce optically active Shiff bases which may be separated as by fractional crystallization. These separate optically active Shiff bases may then be hydrolyzed to form the separate optically active ketones having the structures:

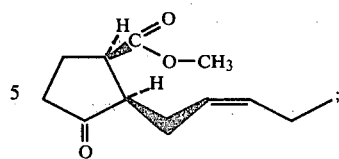;

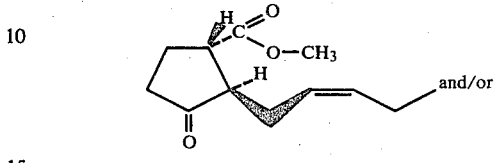 and/or

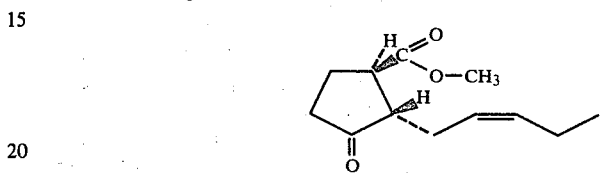

The nor-methyl jasmonate and nitrile of our invention can be used to contribute an intense, green, minty, fresh, clean, floral/jasmine-like aroma to perfumes, perfumed articles and colognes. (Samples of perfumed articles are anionic, cationic, nonionic and zwitterionic solid or liquid detergents, fabric softeners including dryer-added fabric softener articles and fabric softener compositions). As olfactory agents, the nor-methyl jasmonate and nitrile of our invention can be formulated into or used as components of a "perfume composition" or can be used as components of a "perfumed article" or the perfume composition may be added to "perfumed articles".

The term "perfume composition" is used herein to mean a mixture of organic compounds including, for example, alcohols, aldehydes, ketones other than the nor-methyl jasmonate and nitrile of our invention, nitriles, ethers, lactones, natural essential oils, synthetic essential oils and frequently hydrocarbons which are admixed so that the combined odors of the individual components produce a pleasant or a desired fragrance. Such perfume compositions usually contain: (a) the main note or the "bouquet" or foundation stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the nor-methyl jasmonate and nitrile of this invention which will be effective in perfume compositions depends on many factors, including the other ingredients, their amounts and the effects which are desired. It has been found that perfume compositions containing as little as 0.5% of the nor-methyl jasmonate and nitrile of our invention or even less can be used to impart or augment interesting green, minty, fresh, clean, floral/jasmine-like aroma nuances to soaps, liquid and solid cationic, anionic, nonionic and zwitterionic detergents, cosmetics, powders, liquid and solid fabric softeners, dryer-added fabric softener articles, optical brightener compositions and other products. The amount employed can range up to 50% or more and will depend on considerations of cost, nature of the end product and the effect desired on the finished product and particular fragrance sought.

The nor-methyl jasmonate and nitrile of our invention can be used alone or in a perfume composition as an olfactory component in detergents and soaps, space odorants and deodorants; perfumes; colognes, toilet waters; bath salts; hair preparations; such as lacquers, brilliantines, pomades and shampoos; cosmetic preparations, such as creams, deodorants, hand lotions and sun screens; powders, such as talcs, dusting powders, face powders and the like. When used as an olfactory component of a perfumed article such as a cationic, nonionic, anionic or zwitterionic solid or liquid deterfent, as little as 0.01% of the nor-methyl jasmonate and nitrile will suffice to impart an interesting green, minty, fresh, clean, floral/jasmine-like aroma. Generally, no more than 0.9% is required.

In addition, the perfume composition can contain a vehicle or carrier for the nor-methyl jasmonate and nitrile alone or with other ingredients. The vehicle can be a liquid, such as non-toxic alcohol, such as ethanol, a glycol, such as propylene glycol or the like. The carrier can be an absorbent solid, such as a gum or components for encapsulating the composition, such as gelatin which can be used to form a capsul wall surrounding the perfume oil as by means of coacervation.

In addition to its used in perfumery, perfumed articles or colognes in augmenting or enhancing the aroma of perfumes, perfumed articles and colognes, the nor-methyl jasmonate of our invention having the structure:

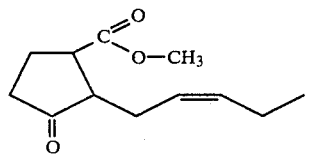

can be reduced as by hydrogenation to form dihydro nor-methyl jasmonate having the structure:

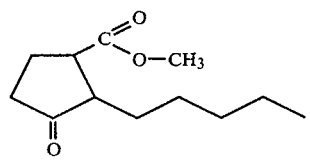

according to the reaction:

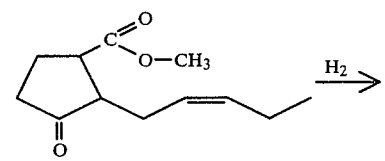

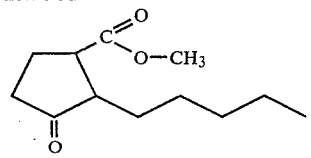

The dihydro nor-methyljasmonate has an excellent jasmine aroma insofar as its use in perfumery and in augmenting or enhancing the aroma of perfumed articles, such as, solid and liquid nonionic, anionic, cationic and zwitterionic detergents as well as fabric softeners, including dryer-added fabric softener articles (e.g., "BOUNCE" ® manufactured by the Procter & Gamble Company of Cincinnati, Ohio). The dihydro normethyl jasmonate has an interesting jasmine/lactone aroma and taste making it useful for augmenting or enhancing the flavor of tropical fruits at levels of from about 0.1 ppm up to about 0.6 ppm. When combined with methyl jasmonate in a 50:50 (weight:weight) mixture or in mixtures of from 3:7 up to 7:3 dihydro nor-methyl jasmonate:methyl jasmonate, the resulting material provides an excellent musky flavoring note useful in pear and peach flavors.

The hydrogenation of nor-methyl jasmonate having the structure:

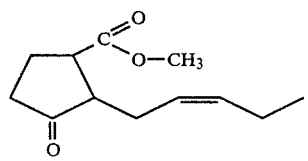

may be carried out totally to produce all dihydro nor-methyl jasmonate having the structure:

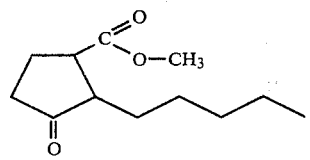

or may be carried out in a controllable fashion whereby mixtures of nor-methyl jasmonate and dihydro nor-methyl jasmonate are produced. The mixture resulting from the hydrogenation of nor-methyl jasmonate in a controlled manner produces materials having excellent flavor and fragrance properties in the jasmine and musk aroma classification. Thus, a 50:50 mixture of nor-methyl jasmonate and dihydro nor-methyl jasmonate gives rise to an excellent jasmine/lactone aroma and taste profile making it useful for augmenting or enhancing the aroma or taste of tropical fruit-flavored foodstuffs, for example, guava nectar. Thus, addition at the level of 0.1 up to 0.5 ppm of the 50:50 mixture of nor-methyl jasmonate:dihydro nor-methyl jasmonate produced by means of controllable hydrogenation of nor-methyl jasmonate over a palladium-on-calcium carbonate catalyst for four hours improves the "natural-like" guava character of guava nectar.

The reaction of nor-methyl jasmonate with hydrogen may take place in the presence of a hydrogenation catalyst which may be either of:

(a) Raney nickel;

(b) Palladium-on-carbon; or
(c) Palladium-on-calcium carbonate (Lindlar Catalyst)
at a temperature in the range of from about 10° C. up to about 100° C.; a hydrogen pressure in the range of from about 5 psig up to about 80 psig, the concentration of catalyst based on weight of starting material, nor-methyl jasmonate being from about 0.1% up to about 10%; then recovering the chemical from the reaction mass. The percentage of palladium in the catalyst may vary from 2% up to 6% with a preferred percentage of palladium-on-carbon or palladium-on-calcium carbonate being about 5%. The reaction may take place in a solvent or may take place in the absence of solvent. When a solvent is used, it is to be inert and easily separable from the reaction mass. Examples of such solvents are n-hexane and n-octane and n-nonane. The time of reaction may vary and depends upon the amount of hydrogenation desired. Thus, when the reaction is carried out for a period of 2-3 hours at about 60° C. and a hydrogen pressure of about 40 psig, a 50:50 mixture of nor-methyl jasmonate:dihydro nor-methyl jasmonate will be produced.

The following examples serve to illustrate our invention and this invention is to be considered restricted thereto only as indicated in the appended claims.

All parts and percentages given herein are by weight unless otherwise specified.

EXAMPLE A

Preparation of Cis-Pent-2-Enyl-1-Chloride

Reaction:

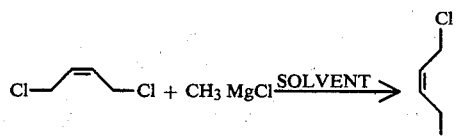

Into a dry 2 liter reaction flask equipped with condenser, addition funnel, stirrer, thermometer and thermo-watch are placed 140 grams of cis-1,4-dichloro-butene-2; 350 grams of tetrahydrofuran (400 ml.).

Over a 25 minute period of solution of 3 moles of methyl magnesium chloride in 350 ml tetrahydrofuran is added from the addition funnel to the reaction mass. After the addition of the methyl magnesium chloride solution, the reaction mass is stirred while progress of the reaction is monitored on GLC apparatus (conditions: 5% Carbowax column programmed at 50°-220° C. at 6° C. per minute). After 15 minutes the ratio of cis-pent-2-enyl-1-chloride: cis-1,4-dichloro-butene-2 is 19.5:76.0. After 1.5 hours the ratio is 41.3:57.3. After 2.5 hours the ratio is 60.4:38.7.

Over a 25 minute period, methyl magnesium chloride (a 3 molar solution in 100 ml tetrahydrofuran) is added to the reaction mass. 3 hours after the second addition, the ratio of product: starting material is 91.6:7.3.

Over a 15 minute period, saturated aqueous ammonium chloride solution is added to the resulting product (400 ml). The reaction mass is stirred for a period of 30 minutes and 300 ml water is added thereto causing suspended solids to dissolve. The reaction mass is then washed with four 200 ml volumes of saturated sodium chloride solution. The reaction mass is then stripped of solvent and distilled after adding thereto 10 grams of Primol ® (registered trademark of Exxon Corporation of Linden, New Jersey, identifying a hydrocarbon mineral oil) yielding the following fractions:

| No. | Vapor Temp. | Liquid Temp. | Vac. mm Hg | Wt. g. | Reflux Ratio |
|---|---|---|---|---|---|
| 1 | 22-26 | 33-43 | 100 | 9.1 | 4:1 |
| 2 | 47 | 58 | 100 | 4.1 | 4:1 |
| 3 | 54 | 64 | 125 | 6.1 | 4:1 |
| 4 | 55 | 65 | 125 | 9.0 | 4:1 |
| 5 | 55 | 70 | 125 | 10.0 | 4:1 |
| 6 | 56 | 79 | 125 | 11.0 | 4:1 |
| 7 |  | 25 | 125 | 3.0 | 4:1 |
| 8 | 45 | 93 | 5 | 6.2 | 4:L |

Fraction 6 is analyzed using NMR and IR analysis. Fractions 4-7 are bulked and used in the following examples.

EXAMPLE B

Preparation of Desmethyl-Cis-Jasmone

Into a 250 ml reaction flask equipped with heating mantle, condenser, stirrer, thermometer and addition funnel is placed a solution of 21.3 grams of sodium hydroxide and 21.3 grams of water. Twenty grams of toluene and 1.5 grams of tricapryl methyl ammonium chloride (ALIQUAT 336 ®, produced by the General Mills Chemicals, Inc.) are then added to the mixture. The reaction mass is then heated to reflux (102° C.) and, over a one-hour period, a mixture of 35 grams of cis-pent-2-enyl-1-chloride (produced according to Example A, bulked fractions 4-7) and 24.5 grams of 2-cyclopentenone is added to the reaction mass while refluxing. The reaction mass is then refluxed for an additional 4-hour period, after which time it is mixed with 100 ml cold water and transferred to a separatory funnel.

The organic layer is separated, washed neutral and the solvent stripped off.

The residual oil is then retained for admixture with the reaction product of Example C prior to distillation.

EXAMPLE C

Preparation of Desmethyl-Cis-Jasmone

Into a 1 liter reaction flask equipped with heating mantle, condenser, thermometer, addition funnel and stirrer is placed a solution of 106.5 grams of sodium hydroxide in 106.5 grams of water. 100 Grams of toluene and 7.5 grams of tricapryl methyl ammonium chloride are then added to the mixture. The mixture is heated to reflux and over a one-hour period, a mixture of 122.5 grams of 2-cyclopentenone and 175 grams of cis pent-2-enyl-1-chloride (produced according to Example A), bulked fractions 4-7) is added to the reaction mass. The reaction mass is then refluxed for a period of two hours, after which time 250 ml water is added thereto and the resulting mixture is transferred to a separatory funnel.

The organic layer is separated, washed neutral and the solvent is stripped off.

The residual oil is then bulked with the product of Example B and the resulting product is combined with 17 grams of Primol ®, 7 grams of triethanolamine and rushed over.

NMR, IR and mass spectral analyses yield the result that the product is desmethyl-cis-jasmone having the structure:

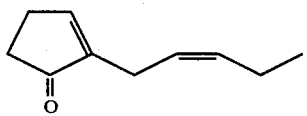

EXAMPLE I (A)

Preparation of
2-(2-Cis-Pentenyl)-3-Cyanocyclopentanone

Reaction:

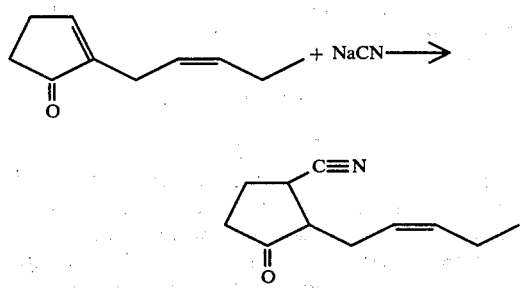

Into a 500 ml reaction flask equipped with mechanical stir, immersion thermometer, water cool bubble condenser, 150 ml addition funnel and heating mantle is placed 10 grams (0.07 moles) of 2-(2-cis-pentenyl)-3-cyclopenten-1-one prepared according to Example B; (0.07 moles); 4.20 grams of glacial acetic acid (0.07 moles) and 245 ml of 95% aqueous ethanol. The reaction mass is heated to 35° C. and, dropwise with stirring while keeping the temperature between 35° and 37° C., 6.86 grams (0.14 moles) of sodium cyanide (dissolved in 75 ml water) is added. After addition, the reaction mass is stirred at a temperature of 35° C. for a period of 3.5 hours.

The ethyl alcohol is then stripped off on a rotary evaporator and the organic layer is taken up in anhydrous diethyl ether. The water phase is extracted with two volumes of diethyl ether and all the organic layers are combined and washed with one volume of saturated sodium chloride solution, two volumes of 5% sodium carbonate solution and 3 volumes of saturated sodium chloride solution. The organic layers are then dried over anhydrous sodium sulfate and concentrated to yield 12.50 grams of crude material. This material is then distilled on a 6" Vigreaux column under vacuum into 4 fractions as follows:

| Fraction No. | Weight | % Product | Weight of Product |
|---|---|---|---|
| 1 | 0.54 | — | — |
| 2 | 0.90 | 69.29 | 0.62 |
| 3 | 5.20 | 98.98 | 5.15 |
| 4 | 1.74 | 78.24 | 1.71 |

The total yield of product is 7.4 grams and the percent yield is 60.37%.

EXAMPLE I(B)

Preparation of Nor-Methyl Jasmonate

Reaction:

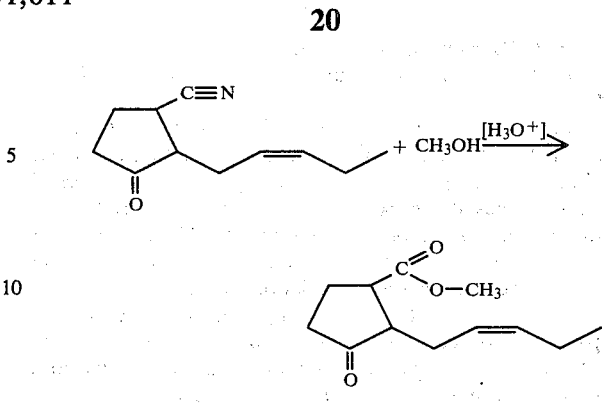

Into a 50 ml two-neck reaction flask equipped with magnetic stirrer, water cooled bubble condenser, immersion thermometer and heating mantle are placed 7.48 grams (0.04 moles) of 3-cyano-2-(2-cis-pentenyl)-cyclopentanone produced according to Example I(A); 7.60 grams (0.04 moles) of para toluene sulfonic acid; and 1.50 grams (0.05 moles) of anhydrous methyl alcohol. The reaction mixture is stirred and heated to reflux (112° C.) and refluxed for six hours. The reaction mass is then cooled and poured onto 250 ml of an ice/water mixture. The resulting organic layer is taken up in diethyl ether and the aqueous layer extracted with two volumes of diethyl ether. The ether layers are combined, washed with saturated sodium chloride solution, and then with two volumes of diethyl ether. The ether layers are combined, washed with saturated sodium chloride solution and then with one volume of 5% sodium carbonate solution and then with two volumes of saturated salt solution. The resulting organic layer is dried over anhydrous sodium sulfate and concentrated to yield 6.10 grams of crude material.

Figure 1:
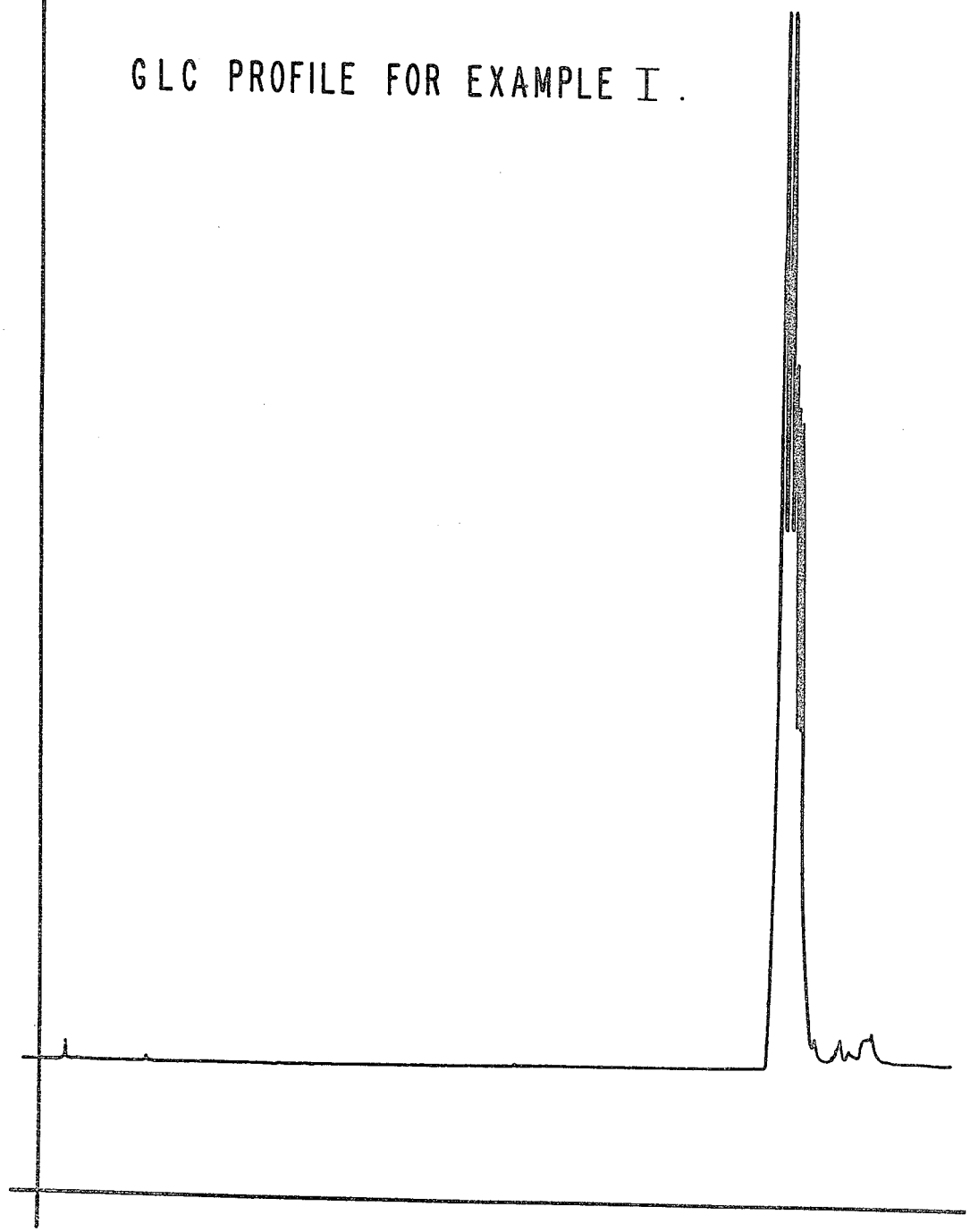
FIG. 1 sets forth the GLC profile for the reaction product of Example I containing nor-methyl jasmonate having the structure.

The resulting cride is subjected to GLC on a 400'×0.032" glass SE-30 capillary column programmed at 100°-190° C. at 3° C. per minute. The GLC profile is set forth in FIG. 1. The NMR spectrum for the resulting nor-methyl jasmonate is set forth in FIG. 2. The infrared spectrum for the resulting nor-methyl jasmonate is set forth in FIG. 3. The mass spectrum for the resulting nor-methyl jasmonate is set forth in FIG. 4.

EXAMPLE II

Isolation of Carbonyls in Jasmine Absolute Via girard-T Reagent

Into a three liter reaction flask equipped with mechanical stirrer, immersion thermometer, nitrogen purge and bubbler, water cooled bubble condenser and 45/50 "Y" adapter is placed 100 grams of jasmine absolute pure; 1000 ml absolute methyl alcohol; 2.0 grams Amberlite R IRC-50 acid ion exchange resin (manufactured by the Rohm & Haas Corporation of Philadelphia, Pa.) and 16.0 grams of Girard's-T reagent ((carboxymethyl) trimethyl ammonium chloride hydrazide). The resulting mixture is heated to reflux under nitrogen atmosphere with stirring. The mixture is refluxed for four hours and the reaction mass is then cooled to room temperature. Three-fourths of the methanol is then stripped off at about 30° C. and 400 ml of water is then added.

The resulting aqueous layer is extracted with five volumes of diethyl ether, saturated with sodium chloride and extracted two more times with diethyl ether. The resulting ether layer is washed with two volumes of saturated sodium chloride solution and dried over anhydrous sodium sulfate and concentrated to 100 ml volume. The resulting material is labeled "non-carbonyls" and set aside.

The aqueous layer is again concentrated to remove all methanol. 100 ml of concentrated HCl is then added and the mixture stirred for thirty minutes at room temperature. The resulting mixture is then extracted with three volumes of diethyl ether. The ether layer is then washed with saturated sodium chloride solution; then sodium bicarbonate solution and saturated salt solution; then dried over anhydrous sodium sulfate and concentrated on a Kuderna-Danish evaporative concentrator apparatus to about 50 ml. The remaining 50 mls is concentrated by nitrogen blowing to yield 1.3874 grams of material labeled "jasmine absolute carbonyls".

A small aliquot of the carbonyls is spiked with methyl jasmonate, nor-methyl jasmonate and 2-(2-cis-pentenyl)-cyclopentenone-1. The spiked material is then passed through a GLC column ($\frac{1}{8}''$ SE-30 column) and compared with the "unspiked" material run under the same conditions. The only common peaks between the spiked and unspiked material were those of nor-methyl jasmonate and this was confirmed according to MS spectra. It was concluded that nor-methyl jasmonate is present in jasmine absolute carbonyls.

FIG. 5 sets forth the GLC trapping on the Carbowax 20-M column for the jasmine absolute carbonyls. FIG. 6 is the mass spectrum for nor-methyl jasmonate trapped out from the Carbowax 20-M GLC column. FIG. 7 is the GLC profile for the SE-30 column containing the nor-methyl jasmonate in the jasmine absolute carbonyls produced according to Example II. FIG. 8 sets forth the mass spectrum for nor-methyl jasmonate trapped out from the GLC SE-30 column containing the jasmine absolute carbonyls.

EXAMPLE III

Perfumed Liquid Detergent

Concentrated liquid detergents (Lysine salt of n-dodecylbenzene sulfonic acid as more specifically described in U.S. Pat. No. 3,948,818 issued on April 6, 1976) with jasmine/floral nuances are prepared containing 0.10%, 0.15%, 0.20%, 0.30% and 0.40% of nor-methyl jasmonate produced according to Example I(B). They are prepared by adding and homogeneously mixing the appropriate quantity of nor-methyl jasmonate prepared according to Example I(B) in the liquid detergent. The detergents all possess excellent jasmine/floral aromas, the intensity increasing with greater concentrations of nor-methyl jasmonate produced according to Example I(B).

EXAMPLE IV

Preparation of A Cologne and Handkerchief Perfume

Nor-methyl jasmonate prepared according to Example I(B) is incorporated into a cologne at concentrations of 2.0%, 2.5%, 3.0%, 3.5%, 4.0%, 4.5% and 5.0% in 80%, 85%, 90% and 95% aqueous food grade ethanol; and into a handkerchief perfumes at concentrations of 15%, 20%, 25% and 30% (in 90% and 95% aqueous food grade ethanol solutions). A distinct and definite jasmine/floral aroma is imparted to the cologne and to the handkerchief perfume at all levels indicated above.

EXAMPLE V

Preparation of A Soap Composition

One hundred grams of soap chips prepared by chopping up a soap prepared as follows according to Japanese Patent 79/28846 assigned to Kawaken Fine Chemicals Company:

"Fatty acid monoisopropanolamide ethoxylate 30 pts. and $P_2O_3$2.5 pts. are reacted and the product is combined with triethanolamine phosphate and a basic soap material and made into soap cakes"

are mixed with one gram of nor-methyl jasmonate until homogeneous compositions are obtained. In each of the cases, the homogeneous compositions are heated under three atmospheres pressure at 180° C. for a period of three hours and the resulting liquids are placed into soap molds. The resulting soap cakes, on cooling, manifest floral and jasmine-like aromas.

EXAMPLE VI

Preparation of a Solid Detergent Composition

A detergent is prepared from the following ingredients according to Example I of Canadian Pat. No. 1,007,948:

| Ingredients | Percent by Weight |
| --- | --- |
| "Neodol 45-11" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed with 0.15 grams of nor-methyl jasmonate prepared according to Example I(B). The detergent sample has an excellent jasmine/floral aroma.

EXAMPLE VII

Jasmine Perfume

The following mixture is prepared:

| Ingredient | Parts by Weight |
| --- | --- |
| Para Cresol | 1 |
| Acetyl Methyl Anthranilate | 20 |
| Farnesol | 4 |
| Cis-3-hexenyl benzoate | 30 |
| Nerolidol | 30 |
| Indol | 15 |
| Eugenol | 20 |
| Benzyl Alcohol | 40 |
| Methyl Linoleate | 40 |
| Jasmine Lactone | 20 |
| Dihydromethyl Jasmonate | 10 |
| Linalool | 150 |
| Benzyl Acetate | 400 |
| Abietyl Alcohol | 150 |
| Nor-methyl Jasmonate | 20 |
| Cis-Jasmone | 50 |

The nor-methyl jasmonate contributes an intense natural jasmine-like nuance to this jasmine formulation. The cis jasmone imparts to this jasmine formulation a green, sweet, celery-like note which is also important to the jasmine perfume formulation.

The combination of cis-jasmone and nor-methyl jasmonate in ratios of from 1:9 up to 9:1 (cis jasmone:nor-methyl jasmonate) imparts a very interesting natural jasmine-like aroma to this perfume formulation as well as other perfume formulations encompassed by our invention.

EXAMPLE VIII

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolve Paper")
2. Adogen 448 (m.p. about 140° F.) as the substrate coating; and
3. An outer coating having the following formulation: (m.p. about 150° F.):
    57 percent $C_{20-22}$ HAPS
    22 percent isopropyl alcohol
    20 percent antistatic agent
    1 percent of the composition of matter of our invention as set forth in the Table I below and giving rise to the aroma nuances as set forth in said Table I below:

TABLE I

| NAME OF COMPOUND | FRAGRANCE CHARACTERISTICS |
|---|---|
| Nor-methyl jasmonate produced according to Example I(B) | A natural jasmine/floral aroma |
| Mixtures of cis-jasmone and nor-methyl jasmonate from 1:9 up to 9:1 cis-jasmone:nor-methyl jasmonate | Natural jasmine/floral, green, sweet, celery aromas with intense green undertones |
| Perfume composition of Example VII | Natural jasmine aroma |

Fabric-softening compositions prepared as set forth above having the aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table I above are imparted in a pleasant manner to the head space in the dryer on operation thereof using the said dryer added fabric softening nonwoven fabric.

EXAMPLE IX

Preparation of Cosmetic Soap

In accordance with Japanese Pat. No. 79/028846 fatty acid monoisopropanolamide ethoxylate (30 parts) and $P_2O_3$ (2.5 parts) are reacted and the product is combined with triethanolamine and 0.5 parts of the perfume composition of Example VII and a basic soap material is made into soap cakes. The resulting soap cakes have a pleasing jasmine/floral aroma.

EXAMPLE X

Liquid Washing Detergent

A liquid washing detergent with mild foaming action is prepared according to Japanese Pat. No. 79/028847 wherein 12 weight percent of polyoxyethylene-2-butyl octyl ether sulphate having the formula 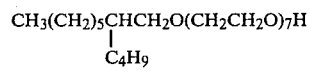 $CH_3(CH_2)_5CH-(C_4H_9)CH_2O(CH_2CH_2O)_8SO_3K$ and 14 percent of dimethyl cetyl amine oxide and 12 percent dimethyl alkyl betaine and 0.4 percent of the perfume composition of Example VII containing nor-methyl jasmonate. The resulting liquid dishwashing detergent with mild foaming action has an interesting pleasant floral/jasmine aroma.

EXAMPLE XI

Low Foam Detergent

A low foam detergent containing the ethylene oxide addition compound of 2-butyloctyl alcohol having the formula:

$$CH_3(CH_2)_5\underset{\underset{C_4H_9}{|}}{C}HCH_2O(CH_2CH_2O)_7H$$

Also in this detergent is 0.4% of the perfume formulation of Example VII. The resulting low foam detergent has an excellent jasmine/floral aroma and is prepared according to Japanese Pat. No. 79/28848 assigned to the Kao Soap Company.

EXAMPLE XII

Anionic Builder Free Liquid Detergent Composition

An anionic builder free liquid detergent composition containing a synergistic combination of quaternary ammonium cationic surfactant and polyethylene oxide non-ionic surfactant and the perfume composition of Example VII is prepared according to Japanese Pat. No. 79/028849 assigned to Kao Soap Company. The composition contains a cationic surfactant of the formula:

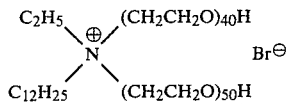

and a nonionic surfactant of the formula:

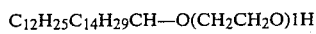

$C_{12}H_{25}C_{14}H_{29}CH-O(CH_2CH_2O)_1H$

To this material is added 0.8% by weight of the perfume formulation of Example VII. The resulting liquid detergent composition has a strong jasmine/floral aroma.

EXAMPLE XIII

Perfumed Liquid Detergent

Concentrated liquid detergents (Lysine salt of n-dodecylbenzene sulfonic acid as more specifically described in U.S. Pat. No. 3,948,818 issued on Apr. 6, 1976) with green, minty, jasmine/floral, fresh, clean nuances are prepared containing 0.10%, 0.15%, 0.20%, 0.30% and 0.40% of the nitrile produced according to Example I(A). They are prepared by adding and homogeneously mixing the appropriate quantity of nitrile prepared according to Example I(A) in the liquid detergent. The detergents all possess excellent green, minty, jasmin/floral, clean, fresh aromas, the intensity increasing with greater concentrations of nitrile produced according to Example I(A).

EXAMPLE XIV

Preparation of a Cologne and Handkerchief Perfume

The nitrile prepared according to Example I(A) is incorporated into a cologne at concentrations of 2.0%, 2.5%, 3.0%, 3.5%, 4.0%, 4.5% and 5.0% in 80%, 85%, 90% and 95% aqueous food grade ethanol; and into handkerchief perfumes at concentrations of 15%, 20%, 25% and 30% (in 90% and 95% aqueous food grade ethanol solutions). Distinct and definitive green, minty, jasmine/floral, clean, fresh aromas are imparted to the colognes and to the handkerchief perfumes at all levels indicated above.

EXAMPLE XV

Preparation of Soap Compositions

One hundred grams of soap chips prepared by chopping up a soap prepared as follows according to Japanese Pat. No. 79/28846 assigned to Kawaken Fine Chemicals Company:

"Fatty acid monoisopropanolamide ethoxylate 30 pts. and $P_2O_3$ 2.5 pts. are reacted and the product is combined with triethanolamine phosphate and a basic soap material and made into soap cakes"

are mixed with one gram of nitrile produced according to Example I(A) until homogeneous compositions are obtained. In each of the cases, the homogeneous compositions are heated under three atmospheres pressure at 180° C. for a period of three hours and the resulting liquids are placed into soap molds. The reulting soap cakes, on cooling, manifest green, minty, floral, fresh, clean and jasmine-like aromas.

EXAMPLE XVI

Preparation of a Solid Detergent Composition

A detergent is prepared from the following ingredients according to Example I of Canadian Pat. No. 1,007,948:

| Ingredients | Percent by Weight |
| --- | --- |
| "Neodol 45-11" (a $C_{14}$-$C_{15}$ alcohol ethoxylated with 11 moles of ethylene Oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is mixed with 0.15 grams of the nitrile prepared according to Example 1(A). The detergent sample has an excellent green, minty, jasmine/floral, fresh, clean aroma.

EXAMPLE XVII

Jasmine perfume having clean, fresh and green, minty nuances is prepared:

| Ingredient | Parts by Weight |
| --- | --- |
| Para Cresol | 1 |
| Acetyl Methyl Anthranilate | 20 |
| Farnesol | 4 |
| Cis-3-hexenyl benzoate | 30 |
| Nerolidol | 30 |
| Indol | 15 |
| Eugenol | 20 |
| Benzyl Alcohol | 40 |
| Methyl Linoleate | 40 |
| Jasmine Lactone | 20 |
| Dihydromethyl Jasmonate | 10 |
| Linalool | 150 |
| Benzyl Acetate | 400 |
| Abietyl Alcohol | 150 |
| Nitrile prepared according to Example I(A) | 20 |
| Cis-Jasmone | 50 |

The nitrile contributes an intense clean, fresh, jasmine/floral, green, minty nuance to this jasmine formulation. The cis-jasmone imparts to this jasmine formulation a green, sweet, celery-like note which is also important to the jasmine formulation especially when it is used in laundry detergent or fabric softener compositons for after the laundering process, the intense perfumey nuance is not present as when using methyl jasmonate and, in addition, the "laundry dryer" aroma is covered.

The combination of cis-jasmone and nitrile prepared according to Example I(A) in ratios of from 1:9 up to 9:1 (cis-jasmone:nitrile) imparts a very interesting natural jasmine aroma with green, minty nuances and clean, fresh nuances to this perfume formulation as well as other perfume formulations encompassed by our invention.

EXAMPLE XVIII

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper")
2. Adogen 448 (m.p. about 140° F.) as the substrate coating; and
3. an outer coating having the following formulation: (m.p. about 150° F.)
   57 percent $C_{20\text{-}22}$HAPS
   22 percent isopropyl alcohol
   20 percent antistatic agent
   1 percent of the composition of matter of our invention as set forth in Table II below and giving rise to the aroma nuances as set forth in Table II below:

TABLE II

| Name of Compound | Fragrance Characteristics |
| --- | --- |
| Nitrile produced according to Example I(A) | A green, minty, natural jasmine/floral, clean, fresh aroma |
| Mixtures of cis-jasmone and nitrile produced according to Example I(A) from 1:9 up to 9:1 cis-jasmone:nitrile | Natural jasmine, green, minty, jasmine/floral, sweet, celery, fresh, clean aromas with intense green undertones |
| Perfume composition of Example XVII | Natural jasmine aroma with clean, fresh, green, minty nuances |

Fabric-softening compositions prepared as set forth above having the aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table II above are imparted in a pleasant manner to the head space in the dryer on operation thereof using the said dryer-added fabric softening nonwoven fabric.

EXAMPLE XIX

Preparation of Cosmetic Soap

In accordance with Japanese Pat. No. 79/028846 fatty acid monoisopropanolamide ethoxylate (30 parts) and $P_2O_3$ (2.5 parts) are reacted and the product is combined with triethanolamine and 0.5 parts of the perfume composition of Example XVII and a basic soap material is made into soap cakes. The resulting soap cakes have a pleasing green, minty, jasmin/floral, clean, fresh aroma.

EXAMPLE XX

Liquid Washing Detergent

A liquid washing detergent with mild foaming action is prepared according to Japanese Pat. No. 79/028847 wherein 12 weight percent of polyoxyethylene-2-butyl octyl ether sulphate having the formula $CH_3(CH_2)_5CH-(C_4H_9)CH_2CH_2O)_8SO_3K$ and 14 percent of dimethyl cetyl amine oxide and 12 percent dimethyl alkyl betaine and 0.4 percent of the perfume composition of Example XVII containing the nitrile of Example I(A). The resulting liquid dishwashing detergent with mild foaming action has an interesting green, minty, floral/jasmine, clean, fresh aroma.

EXAMPLE XXI

Low Foam Detergent

A low foam detergent containing the eithylene oxide addition compound of 2-butyloctyl alcohol having the formula:

$$CH_3(CH_2)_5\underset{\underset{C_4H_9}{|}}{C}HCH_2O(CH_2CH_2O)_7H$$

Also in this detergent is 0.4% of the perfume formulation of Example XVII. The resulting low foam detergent has an excellent green, minty, jasmine/floral, clean, fresh aroma and is prepared according to Japanese Pat. No. 79/28848 assigned to the Kao Soap Company.

EXAMPLE XXII

Anionic Builder Free Liquid Detergent Composition

An anionic builder free liquid detergent composition containing a synergistic combination of quaternary ammonium cationic surfactant and polyethylene oxide nonionic surfactant and the perfume composition of Example XVII is prepared according to Japanese Pat. No. 79/028849 assigned to Kao Soap Company. The composition contains a cationic surfactant of the formula:

$$\begin{array}{c}C_2H_5 \\ \diagdown \\ \diagup \overset{\oplus}{N} \diagdown \\ C_{12}H_{25} \end{array} \begin{array}{c}(CH_2CH_2O)_{40}H \\ \\ (CH_2CH_2O)_{50}H\end{array} \quad Br^{\ominus}$$

and a nonionic surfactant of the formula:

$$C_{12}H_{25}C_{14}H_{29}CH-O(CH_2CH_2O)_1H$$

To this material is added 0.8% by weight of the perfume formulation of Example XVII. The resulting liquid detergent composition has a strong green, minty, jasmine/floral, clean, fresh aroma compatible with the resulting dry product without the intense objectionable perfumey aroma.

What is claimed is:

1. The nitrile compound having the structure:

[structure of cyclopentanone with C≡N group and pentenyl side chain]

* * * * *